United States Patent
Himmler

(10) Patent No.: US 7,019,166 B2
(45) Date of Patent: Mar. 28, 2006

(54) METHOD FOR THE PRODUCTION OF 2,4,5-TRIMETHYLPHENYL ACETIC ACID

(75) Inventor: Thomas Himmler, Odenthal (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/510,288

(22) PCT Filed: Mar. 27, 2003

(86) PCT No.: PCT/EP03/03180

§ 371 (c)(1),
(2), (4) Date: Apr. 1, 2005

(87) PCT Pub. No.: WO03/084914

PCT Pub. Date: Oct. 16, 2003

(65) Prior Publication Data

US 2005/0182274 A1    Aug. 18, 2005

(30) Foreign Application Priority Data

Apr. 8, 2002   (DE) .............................. 102 15 294

(51) Int. Cl.
  C07C 53/134 (2006.01)
  C07C 53/38 (2006.01)

(52) U.S. Cl. ...................................... 562/496; 562/840
(58) Field of Classification Search ................ 562/405, 562/493, 496, 840, 859
See application file for complete search history.

(56) References Cited

U.S. PATENT DOCUMENTS

| | | | |
|---|---|---|---|
| 3,658,923 A | 4/1972 | Stapp | 260/651 HA |
| 4,369,322 A | 1/1983 | Schalke et al. | 546/330 |
| 6,110,872 A | 8/2000 | Lieb et al. | 504/284 |
| 6,140,358 A | 10/2000 | Lieb et al. | 514/425 |
| 6,271,180 B1 | 8/2001 | Lieb et al. | 504/292 |
| 6,388,123 B1 | 5/2002 | Lieb et al. | 560/76 |
| 6,486,343 B1 | 11/2002 | Lieb et al. | 560/39 |
| 6,511,942 B1 | 1/2003 | Lieb et al. | 504/299 |
| 2001/0004629 A1 | 6/2001 | Lieb et al. | 504/292 |
| 2003/0171219 A1 | 9/2003 | Lieb et al. | 504/221 |

OTHER PUBLICATIONS

J. Prakt Chem., 80 (month unavailable) 1909, pp. 192-200, C. Willgerodt et al, "Darstellung von Suren und Säurearniden aus Phenylalkylketonen durch Behandlung mit gelbem Schwefelammouim".
J. Amer. Chem. Soc., 92 Feb. 25, 1970, pp. 994-998, Daniel T. Longone et al, "Multilayered [2.2]Paracyclophane. Synthesis and Properties".
J. Org. Chem. vol. 33 No. 6, Jun. 1968, pp. 2338-2342, Melvin S. Newman et al, "Free-Radical 1:5 Rearrangement of the Trichloromethyl Group".
J. Org. Chem., Nov. 24, 1959, pp. 1823-1825, R.D. Lake et al, "Chloromethylation of 1,2,4-Trimethylbenzene".
Atti Accad., Lettere Arti Palermo, Pt. I 24 (month available) 1965, pp. 19-33, Giuseppe Werber et al, "Ricerche Sugli Acidi Arilacetici. Reattivita' Dei Trimetil-Benzeni Verso I Gliossalati Alchilici in Ambiente Acido".
J. Amer, Chem. Soc., 52, Jul. 1930, pp. 2959-2972, R.W. Maxwell, "Study of the Possible Isomerism of Certain Analogs of Resolvable Diphenyl Compounds.".
J. Prakt. Chemie 2, 41, (month unavailable) 1890, pp. 483-514, Ad Claus, "Zur Kennutuiss der gemischten fettaromatischen Ketone und ihrer Oxydation durch Kaliumpermanganat".
Org. Synthesis 35, (month unavailable) 1955, pp. 11-14, J.J. Klingenberg, "p-Bromomandelic Acid".
*Fisher, C.H. and Walling, C.T.: "The Reaction of Alpha-Dihlaoacetophenones with Alkali" Journal of the American Chemical Society, vol. 57, 1935, pp. 1562-1564, XP002249325.
*Smith, L.I.: Macmullen, C.W.: "the Reaction between Quinones and Sodium Enolates. IV. Pseudocumoquinone, Socium Acetoacetic Ester and Sodium Malonic Ester" Journal of the American Chemical Society, vol. 58, 1936, pp. 629-635, XP002249326.
*Fisher, C.H. et al: The Haloform Reaction. VI. Alpha-Halogen Derivatives of Unhindered Ketones Journal of the American Chemical Society, vol. 54, 1932, pp. 3665-3674, XP002249327.

*Primary Examiner*—Johann Richter
(74) *Attorney, Agent, or Firm*—Richard E. L. Henderson; Raymond J. Harmuth

(57) ABSTRACT

The present invention relates to a novel process for preparing 2,4,5-trimethylphenyl-acetic acid by reacting pseudocumene with dichloroacetyl chloride in a Friedel-Crafts reaction to give 2,2-dichloro-1-(2,4,5-trimethylphenyl)ethanone, converting the 2,2-dichloro-1-(2,4,5-trimethylphenyl)ethanone to 2,4,5-trimethylmandelic acid using an alkali metal hydroxide and reducing the 2,4,5-trimethylmandelic acid to 2,4,5-tri-methylphenylacetic acid.

2 Claims, No Drawings

METHOD FOR THE PRODUCTION OF 2,4,5-TRIMETHYLPHENYL ACETIC ACID

The present patent application has been filed under 35 U.S.C. 371 as a national stage application of PCT/EP03/03180, filed Mar. 27, 2003, which was published in German as International Patent Publication WO 03/084914 on Oct. 16, 2003, which is entitled to the right of priority of German Patent Application 102 15 294.2, filed Apr. 8, 2002.

The present invention relates to a novel process for preparing 2,4,5-trimethylphenylacetic acid.

2,4,5-Trimethylphenylacetic acid is a compound which has already been known for some time (for example from: J. prakt. Chem. 80 (1909) 193; J. Amer. Chem. Soc. 58 (1936) 629–35). The preparation may be effected, for example, by a Willgerodt-Kindler reaction starting from 2,4,5-trimethylphenylacetophenone. However, this method results in large amounts of sulfurous wastes. In addition, highly odorous, volatile sulfur compounds may occur.

A further method starts from 2,4,5-trimethylbenzyl bromide. For example, sodium cyanide is used to prepare the corresponding nitrile which is subsequently hydrolyzed (J. Amer. Chem. Soc. 58 (1936) 629–35; DE-A 19 602 524). This nitrile can also be obtained by reacting durene (1,2,4, 5-tetramethylbenzene) with cyanogen chloride at above 600° C. (DE-A 2 854 210); however, the high toxicity of cyanogen chloride is disadvantageous in this context. The 2,4,5-trimethylbenzyl bromide required may in turn be prepared by brominating durene with N-bromosuccinimide (see, for example, J. Amer. Chem. Soc. 92 (1970) 994–8). However, experience has shown that a disadvantage in this context is that such brominations also lead to polybrominated products, so that complicated purification steps become necessary.

A further possibility which has become known is to start from 2,4,5-trimethylbenzyl chloride, and to prepare the nitrile therefrom (J. Amer. Chem. Soc. 58 (1936) 629–35; J. Org. Chem. 33 (1968) 2338–42) and then hydrolyze it. 2,4,5-Trimethylbenzyl chloride is known and can be prepared by chloromethylating pseudocumene (1,2,4-trimethylbenzene). However, it is to be regarded as extremely unfavorable that the chloromethylation proceeds only with unsatisfactory selectivity. Selectivities of about 75–85% are described (J. Org. Chem. 24 (1959) 1823–5; U.S. Pat. No. 3,658,923). In addition, owing to the possibility that the highly toxic bischloromethyl ether occurs, the chloromethylation is a method which can only be carried out with high technical complexity.

Finally, a further possibility for preparing 2,4,5-trimethylphenylacetic acid is to initially react pseudocumene with glyoxylic acid to give 2,4,5-trimethylmandelic acid (Atti Accad., Lettere Arti Palermo, Pt. I24 (1965) 19–33) and then to reduce it to 2,4,5-trimethylphenylacetic acid (J. Amer. Chem. Soc. 58 (1936) 629–35). However, the preparation of 2,4,5-trimethylmandelic acid by the process specified has the disadvantage that the 2,4,5-trimethylmandelic acid which has already formed reacts with further pseudocumene under the customary reaction conditions and thus forms considerable proportions of 2,2',4,4',5,5'-hexamethyldiphenylacetic acid (Atti Accad., Lettere Arti Palermo, Pt. I24 (1965) 19–33), which of course reduce the yield and make necessary additional purification steps.

All of the methods which have become known hitherto for preparing 2,4,5-trimethyl-phenylacetic acid accordingly have sometimes considerable shortcomings and disadvantages which complicate the preparation of 2,4,5-trimethylphenylacetic acid. Since phenylacetic acids, also including 2,4,5-trimethylphenylacetic acid, are important precursors, for example for active ingredients in crop protection (cf. WO 97/36868), there is a need for a technically simple method for preparing 2,4,5-trimethylphenylacetic acid.

It has now been found that 2,4,5-trimethylphenylacetic acid is surprisingly obtained in a high yield and isomeric purity by initially reacting pseudocumene with dichloroacetyl chloride in a Friedel-Crafts reaction to give 2,2-dichloro-1-(2,4,5-trimethylphenyl)ethanone, and preparing 2,4,5-trimethylmandelic acid from it using an alkali metal hydroxide and finally reducing it to 2,4,5-trimethylphenylacetic acid.

The preparation of mandelic acids by reacting dihaloacetophenones with an alkali metal hydroxide is a known method (see, for example: Org. Syntheses 35 (1955) 11–14). Likewise already known is the bromination of 2,4,5-trimethylphenylethanone (acetylpseudocumene) and/or 2-chloro-1-(2,4,5-trimethylphenyl)ethanone (chloroacetylpseudocumene) to obtain 2,2-dibromo-1-(2,4,5-trimethylphenyl)ethanone and/or 2-bromo-2-chloro-1-(2,4,5-trimethylphenyl)ethanone respectively, and the reaction of these with aqueous potassium hydroxide solution to give 2,4,5-trimethylmandelic acid (J. Amer. Chem. Soc. 57 (1935) 1562–4). However, this method has the disadvantage of having two stages and being complicated.

Dichlorinated acetophenones can be prepared in a likewise two-stage process by Friedel-Crafts acylation of the corresponding aromatic with acetyl chloride and subsequent chlorination.

However, it is more advantageous to react the aromatic in question in a one-stage procedure directly with dichloroacetyl chloride in a Friedel-Crafts acylation to give the dichlorinated acetophenone.

While 2,4,5-trimethylphenylethanone (J. prakt. Chemie <2> 41 (1890) 509; J. Amer. Chem. Soc. 52 (1930) 2959–72) and 2-chloro-1-(2,4,5-trimethylphenyl)ethanone (J. Amer. Chem. Soc. 57 (1935) 1562) have already been known for some time, the 2,2-dichloro-1-(2,4,5-trimethylphenyl)ethanone required to prepare 2,4,5-trimethylphenylacetic acid by the process according to the invention has hitherto not been described.

The reaction of pseudocumene with acetyl chloride under Friedel-Crafts conditions affords 2,4,5-trimethylphenylethanone in high selectivity (see comparative example 1). In contrast, the corresponding reaction with chloroacetyl chloride is distinctly less selective (see Comparative example 2).

It could therefore not have been expected from the outset that the Friedel-Crafts reaction of pseudocumene with dichloroacetyl chloride would afford 2,2-dichloro-1-(2,4,5-trimethylphenyl)ethanone in sufficiently high isomeric purity.

The process according to the invention may be illustrated by the following scheme:

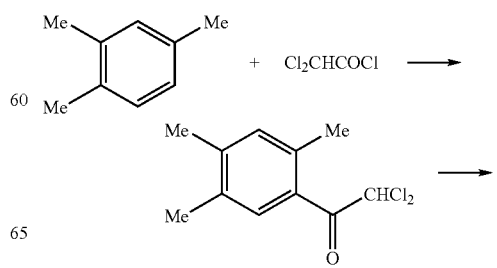

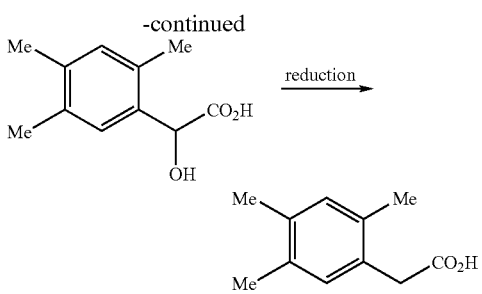

The present invention accordingly likewise provides the novel compound 2,2-dichloro-1-(2,4,5-trimethylphenyl) ethanone.

Surprisingly, 2,4,5-trimethylphenylacetic acid can be prepared by the process according to the invention in a simpler manner, in better selectivity and in better yield than by the processes which have become known before.

2,2-Dichloro-1-(2,4,5-trimethylphenyl)ethanone is prepared by the first step of the process according to the invention by reacting pseudocumene with dichloroacetyl chloride in the presence of a Friedel-Crafts catalyst.

Useful Friedel-Crafts catalysts in the process according to the invention may be, for example, aluminum chloride, iron(III) chloride, tin tetrachloride or zeolites. Preference is given to using aluminum chloride as the Friedel-Crafts catalyst.

The amount of Friedel-Crafts catalyst to be used in the process according to the invention is not critical. For example, from 0.8 to 1.2 mol of catalyst per dichloroacetyl chloride may be used. Preference is given to from 0.9 to 1.1 mol of dichloroacetyl chloride per mole of dichloroacetyl chloride.

Useful solvents for the Friedel-Crafts reaction in the process according to the invention are substantially inert solvents, for example nitrobenzene, carbon disulfide, methylene chloride, 1,2-dichloroethane or pseudo cumene itself. Preference is given to carbon disulfide, 1,2-dichloroethane and pseudo cumene. Particular preference is given to pseudocumene.

The amount of dichloroacetyl chloride to be used in the process according to the invention is not critical and may vary within wide limits. When a solvent is used, for example, from 0.8 to 1.2 mol of dichloroacetyl chloride per mole of pseudocumene may be used. Preference is given to from 0.9 to 1.1 mol of dichloroacetyl chloride per mole of pseudocumene.

When an excess of pseudocumene is used as a solvent, the ratio of dichloroacetyl chloride to pseudocumene will naturally be distinctly smaller.

The first step of the process according to the invention may be carried out at temperatures between −20 and +60° C. Preference is given to temperatures between −10 and +30° C.

The reaction times of the first step of the process according to the invention are between 1 and 24 hours.

The alkali metal hydroxide used in the second step of the process according to the invention may be, for example, NaOH, KOH and CsOH. Preference is given to NaOH and KOH; particular preference is given to NaOH.

The amount of alkali metal hydroxide is from 3 to 7 mol per mole of 2,2-dichloro-1-(2,4,5-trimethylphenyl)ethanone. Preference is given to from 4 to 6 mol per mole of 2,2-dichloro-1-(2,4,5-trimethylphenyl)ethanone.

A useful solvent for the second step of the process according to the invention is water.

The second step of the process according to the invention may be carried out at temperatures between −20 and +120° C. Preference is given to temperatures between +20 and +110° C.

The reaction times of the second step of the process according to invention are between 1 and 24 hours.

The reduction of 2,4,5-trimethylmandelic acid in the third step of the process according to the invention may be carried out by various methods known in principle for reducing mandelic acids, for example by means of hydrogen over suitable catalysts, or by means of red phosphorus. Preference is given to carrying out the reduction with red phosphorus.

The reduction with red phosphorus is effected in the presence of catalytic amounts of iodide, of a solvent and of a strong acid.

In the third step of the process according to the invention, the red phosphorus is used in amounts of from 0.67 to 3 mol per mole of 2,4,5-trimethylmandelic acid. Preference is given to from 1 to 2 mol per mole of 2,4,5-trimethylmandelic acid. Excesses of red phosphorus may be recovered and reused.

The iodide source used in the third step of the process according to the invention may be hydrogen iodide, KI or NaI. In principle, iodine may also be used. Preference is given to using NaI or KI.

The amount of iodide is from 1 to 30 mol percent (based on 2,4,5-trimethylmandelic acid); preference is given to using from 5 to 20 mol percent.

Useful solvents in the third step of the process according to the invention are formic acid, acetic acid, propionic acid, etc., mixtures of these solvents, or from 70 to 85% aqueous phosphoric acid. Preference is given to from 70 to 85% aqueous phosphoric acid and acetic acid; particular preference is given to acetic acid.

The strong acid used in the third step of the process according to the invention is conc. sulfuric acid, conc. hydrochloric acid or from 80 to 85% aqueous phosphoric acid. Preference is given to conc. sulfuric acid and conc. hydrochloric acid. Particular preference is given to conc. hydrochloric acid.

When the solvent used is from 80 to 85% aqueous phosphoric acid, the addition of a further acid may naturally be dispensed with.

The third step of the process according to the invention may be carried out at temperatures between +20 and +120° C. Preference is given to temperatures between +60 and +110° C.

The reaction times of the third step of the process according to the invention are between 1 and 24 hours.

The preparation of 2,4,5-trimethylphenylacetic acid by the process according to the invention is to be illustrated by the following preparative examples:

PREPARATIVE EXAMPLES

Example 1

2,2-Dichloro-1-(2,4,5-trimethylphenyl)ethanone

At 0–5° C., 146.6 g of AlCl$_3$ are introduced in portions into a mixture of 333 g of pseudocumene and 147.7 g of dichloroacetyl chloride within 2–3 hours. Afterward, the mixture is stirred at 0–5° C. for a further 2 hours and allowed to come to room temperature. The reaction mixture is stirred into 3 300 ml of ice-water containing 66.7 g of conc. hydrochloric acid. Extraction is effected once with 350 ml, and twice with 500 ml each time, of ethyl acetate. The combined organic phases are extracted first with 165 ml of water and then 85 ml of saturated aqueous NaCl solution, dried and concentrated (up to bath temperature 70° C./1 mbar). 236.1 g of oil are obtained which, by GC, contain 85.57% of target product (TP)=202.0 g=87.4% of theory. In addition, the following are present: 2.8% of pseudocumene; 2.6% of tetramethylbenzene; 0.57% of isomeric TP; 2.27% of isomeric TP; 0.55% of isomeric TP; 0.72% of isomeric TP; 1.21% of isomeric TP. The sum of isomers of the target product is thus 5.32%; i.e. the ratio of TP to isomers is approx. 94:6.

$^1$H NMR (400 MHz, CDCl$_3$): δ=2.29 (s; 6H), 2.48 (s; 3H), 6.71 (s; 1H), 7.09 (s; 1H), 7.50 (s; 1H) ppm.

MS: m/e=230 (M$^+$ for $^{35}$Cl; approx. 2% rel. intensity), 147 (M-CHCl$_2$, 100%), 119 (Me$_3$Ph; 28%).

Example 2

2,2-Dichloro-1-(2,4,5-trimethylphenyl)ethanone

At 0–5° C., 14.7 g of AlCl$_3$ are introduced in portions into a solution of 28.3 g of pseudocumene and 14.8 g of dichloroacetyl chloride in 100 ml of carbon disulfide within one hour. The mixture is then stirred at 0–5° C. for a further 2 hours, allowed to come to room temperature and stirred for a further 2 hours. 50 ml of 2 N hydrochloric acid are added dropwise to the reaction mixture. Extraction is effected once with 50 ml and twice with 25 ml each time, of ethyl acetate. The combined organic phases are extracted with 50 ml of saturated aqueous NaCl solution, dried and concentrated (bath temperature up to 50° C./1 mbar).

29.51 g of oil are obtained which, by GC, contain 61.49% of target product (TP)=18.1 g=78.3% of theory. In addition, the following are present: 28.9% of pseudocumene; 3.2% of tetramethylbenzene; 0.47% of isomeric TP; 1.58% of isomeric TP; 0.40% of isomeric TP; 0.55% of isomeric TP; 0.82% of isomeric TP. The sum of isomers of the target product is thus 3.82%; i.e. the ratio of TP to isomers is approx. 94:6.

Example 3

2,2-Dichloro-1-(2,4,5-trimethylphenyl)ethanone

The procedure of example 2 is repeated, with the difference that operation is effected in 1,2-dichloroethane as the solvent.

28.87 g of oil are obtained which, by GC, contain 59.15% of target product (TP)=17.1 g=74% of theory. In addition, the following are present: 19.4% of pseudocumene; 5.6% of tetramethylbenzene; 0.96% of isomeric TP; 2.71% of isomeric TP; 0.42% of isomeric TP; 0.52% of isomeric TP; 0.90% of isomeric TP. The sum of isomers of the target product is thus 5.51%; i.e. the ratio of TP to isomers is approx. 91.5:8.5.

Example 4

2,4,5-Trimethylmandelic Acid 222 g of 45% sodium hydroxide solution and 400 ml of water are initially charged and heated to reflux. Within approx. 90 minutes, 115.6 g of 2,2-dichloro-1-(2,4,5-trimethylphenyl)ethanone are added dropwise. Subsequently, the reaction mixture is boiled for a further hour, then admixed at 45° C. with 400 ml of water and at room temperature with 400 ml of MTBE, the phases are separated, the aqueous phase is extracted once again with 300 ml of MTBE, and is then acidified with sulfuric acid and the precipitated solid is filtered off with suction. The solid is then washed three times with 50 ml each time of water and then dried. 102.4 g of white solid are obtained which, by GC, contains 91.9% of target product=94.1 g=96.9% of theory.

Example 5

2,4,5-Trimethylphenylacetic Acid

A mixture of 69.9 g of 2,4,5-trimethylmandelic acid, 38.3 g of 36% hydrochloric acid, 11.2 g of red phosphorus and 6 g of KI in 270 ml of glacial acetic acid is heated to 100° C. for 16 hours. Subsequently, the mixture is diluted at room temperature with 150 ml of glacial acetic acid. The excess of phosphorus is filtered off with suction and washed three times with 50 ml of glacial acetic acid. The filtrate is admixed with 150 ml of water and the acetic acid is substantially removed by rotary evaporation at bath temperature 50° C. 60 mbar. The remaining suspension is adjusted to pH 1 using 5 ml of 20% sulfuric acid and the solid is filtered off with suction. The solid is washed three times with 180 ml of water each time, and this water becomes the first filtrate. This causes solid to precipitate out once again, which is filtered off with suction through the already existing filtercake. The filtercake is washed once more with 100 ml of water and dried to constant weight. This results in 64.46 g of white solid which, by GC, contains 95.8% of target product=61.7 g=96.2% of theory.

COMPARATIVE EXAMPLES

Comparative Example 1

2,4,5-Trimethylphenylethanone

At 0–5° C., 14.7 g of AlCl$_3$ are introduced in portions into a mixture of 60 g of pseudocumene and 7.85 g of acetyl chloride within 1–2 hours. Afterward, the mixture is stirred at 0–5° C. for another 2 hours and allowed to come to room temperature. The reaction mixture is stirred into 340 ml of ice-water containing 7 g of conc. hydrochloric acid. Extraction is effected once with 35 ml, and twice with 50 ml each time, of ethyl acetate. The combined organic phases are extracted first with 20 ml of water and then with 10 ml of saturated aqueous NaCl solution, dried and concentrated (bath temperature of up to 70° C./1 mbar).

14.44 g of oil are obtained which, by GC, contain 89.82% of target product (TP)=12.97 g=80.0% of theory. In addition, the following are present: 2.9% of pseudocumene; 0.5% of tetramethylbenzene; 0.4% of isomeric TP; 1.28% of isomeric TP; 0.49% of isomeric TP; 0.30% of isomeric TP; 0.62% of isomeric TP. The sum of isomers of the target product is thus 3.09%; i.e. the ratio of TP to isomers is approx. 97:3.

Comparative Example 2

2-Chloro-1-(2,4,5-trimethylphenyl)ethanone

At 0–5° C., 88 g of AlCl$_3$ are introduced in portions into a mixture of 170 g of pseudocumene and 67.7 g of chloroacetyl chloride within 2–3 hours. Afterwards, the mixture is stirred at 0–5° C. for another 2 hours and allowed to come to room temperature. The reaction mixture is stirred into 1 000 ml of ice-water containing 20 g of conc. hydrochloric acid. Extraction is effected once with 100 ml, and twice with 75 ml each time, of ethyl acetate. The combined organic phases are extracted first with 100 ml of water and then with 50 ml of saturated aqueous NaCl solution, dried and concentrated (bath temperature of up to 70° C./1 mbar). 125.77 g of oil are obtained which, by GC, contain 65.2% of target product (TP)=82.0 g=69.5% of theory. In addition, the following are present: 6.8% of pseudocumene; 1.8% of tetramethylbenzene; 16.7% of isomeric TP; 8.0% of isomeric TP. The sum of isomers of the target product is thus 24.7%; i.e. the ratio of TP to isomers is approx. 72.5:27.5.

What is claimed is:

1. A process for preparing 2,4,5-trimethylphenylacetic acid comprising
    (a) reacting pseudocumene with dichloroacetyl chloride in a Friedel-Crafts reaction to give 2,2-dichloro-1-(2, 4,5-trimethylphenyl)ethanone,
    (b) converting the 2,2-dichloro-1-(2,4,5-trimethylphenyl) ethanone to 2,4,5-trimethylmandelic acid using an alkali metal hydroxide, and
    (c) reducing the 2,4,5-trimethylmandelic acid to form 2,4,5-trimethylphenylacetic acid.

2. 2,2-Dichloro-1-(2,4,5-trimethylphenyl)ethanone.

* * * * *